United States Patent
Pflaum et al.

(10) Patent No.: US 6,560,799 B1
(45) Date of Patent: May 13, 2003

(54) SUPPORT SYSTEM FOR AN EXAMINATION OR TREATMENT SUBJECT

(75) Inventors: Michael Pflaum, Adelsdorf (DE); Reinhard Zitzmann, Effeltrich (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/677,238

(22) Filed: Oct. 2, 2000

(30) Foreign Application Priority Data

Oct. 1, 1999 (DE) .......................... 199 47 361

(51) Int. Cl.[7] .............................................. A61G 13/00
(52) U.S. Cl. .................................. 5/600; 5/601; 5/86.1
(58) Field of Search ........................ 5/600, 601, 614, 5/618, 86.1, 81.1

(56) References Cited

U.S. PATENT DOCUMENTS 3,814,414 A * 6/1974 Chapa ........................... 5/601

FOREIGN PATENT DOCUMENTS

DE    1 566 416    9/1969
DE    197 51 329    5/1999

* cited by examiner

*Primary Examiner*—Heather Shackelford
*Assistant Examiner*—Fredrick Conley
(74) *Attorney, Agent, or Firm*—Schiff Hardin & Waite

(57) ABSTRACT

A support mechanism system has a mechanism base at which a support plate for accepting a treatment and/or examination subject can be detachably attached, and a transport gurney and at least two support plates that are fixable at the transport gurney. One of the support plates is fashioned as an operation plate for carrying out a surgical intervention at a subject, and the other a radiological support plate having at least one radiation-transparent region. Either plate can be optionally attached to the base by a fastening arrangement that is compatible with both plates. The base also has at least one connector for providing operation support for an implement or component used in a surgical procedure.

13 Claims, 1 Drawing Sheet

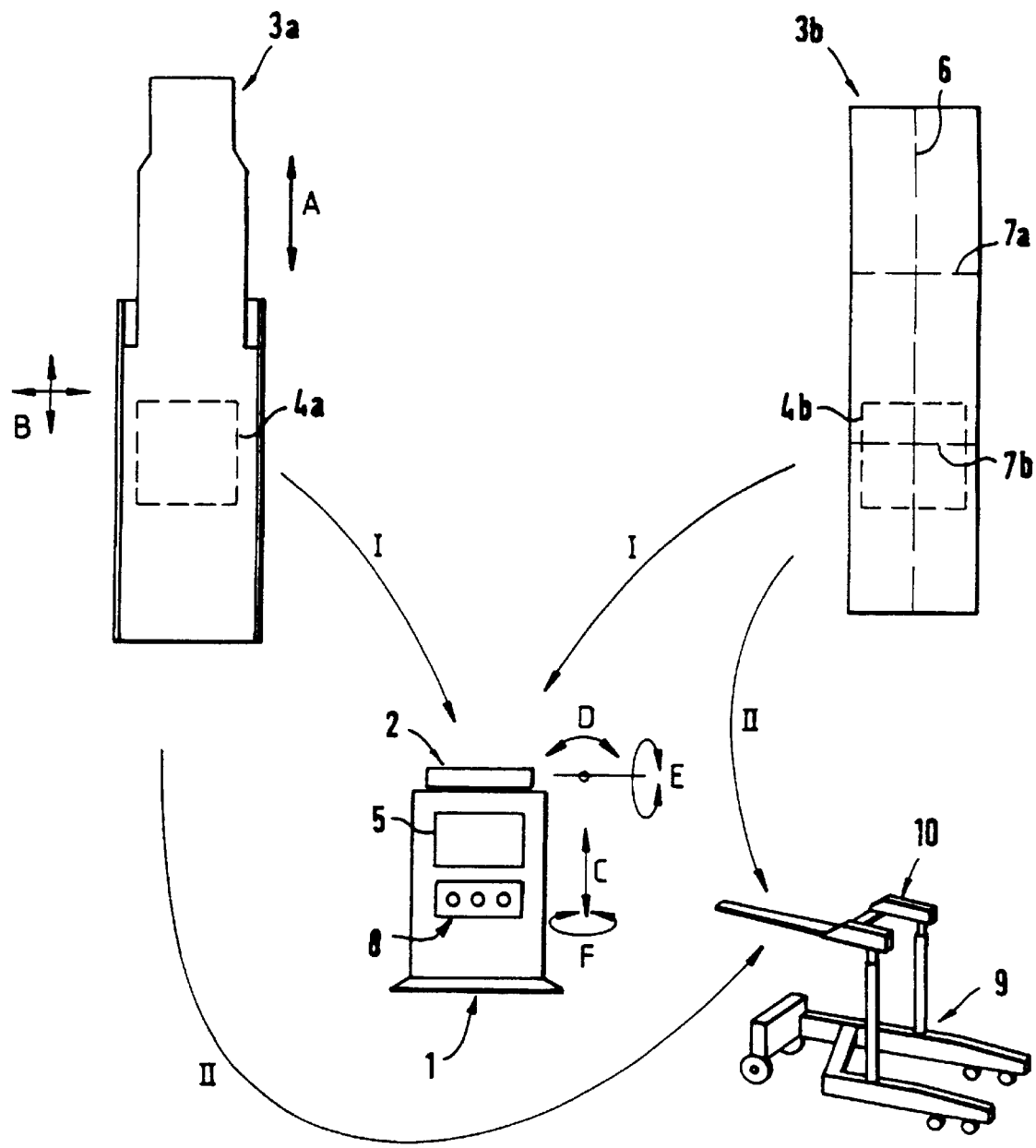

SUPPORT SYSTEM FOR AN EXAMINATION OR TREATMENT SUBJECT

BACKGROUND OF THE INVENTION

1. Field of the Invention

The present invention relates to a support system for an examination subject of the type having a mechanism base onto which a support plate for accepting a treatment and/or examination subject can be detachably attached.

2. Description of the Prior Art

Support mechanism systems of this type are normally utilized in the medical field. The patient to be treated or examined is situated on the support plate in a treatment or examination room. Support plates are known in the form of operation plates. An operation plate is fashioned for carrying out a particular operative intervention at the subject. The operation plate can be fastened via specific fastening elements at the mechanism base that is firmly arranged in the operating room. Normally, the already anaesthetized patient, already lying on the operation plate, is brought from another room by means of a transport gurney into the operating room, where the operation plate is taken from the transport gurney and is fastened at the mechanism base, the operation plate being detachably fastened at said transport gurney for this purpose. However, only operation plates which have appropriate fastening capabilities or which have fastening elements compatible with the fastening elements provided at the mechanism base, can be attached to the mechanism base.

Another known support mechanism system has a support plate that is fashioned as a radiological support plate and that has a more or less large radiation-transparent region making it possible to undertake transillumination exposures of a patient lying on the radiological support plate, using a fluoroscopy device such as an X-ray device. For example, the radiological support plate can be fashioned as an angiography table for that specific application. A radiological support plate is often firmly and detachably connected to the mechanism base; however, when the support plate is detachable, specific fastening means are utilized, which exclusively enable the fastening of such radiological support plates. The mechanism base is also situated in a specifically provided examination room.

The known support mechanism systems have the disadvantage that each system is limited to allowing only certain support plate to be attached to the mechanism base, due to the configuration of the fastening means. For example, when three operation rooms and, for example, two rooms for carrying out radiological examinations are provided in a hospital, considerable difficulties occur when all three operation rooms are occupied simultaneously and an emergency operation must be promptly undertaken. This is not possible in the radiological examination rooms, since the support plates provided there, allow X-ray-diagnostic examinations and also minimally invasive treatments, for example by means of a catheter, but they are not suitable for carrying out operations at an open vessel or cavity, since the hygienic requirements and the device equipment are not sufficient.

SUMMARY OF THE INVENTION

An object of the present invention is to provide a support mechanism system, which is highly flexible, so that aforementioned bottlenecks can be prevented.

For solving this problem with respect to a support mechanism system of the type described above, the inventive support mechanism system includes a transport gurney or cart and at least two support plates that can be fixed at the transport gurney, with one support plate being utilized for carrying out an operative intervention at the subject and the other one being fashioned as a radiological support plate having at least one radiation-transparent area. The plates are optionally attachable by the same fastening arrangement, at the mechanism base, and the base has at least one connector for an implement or component of a medical operating system for examination, treatment or surgery.

The system includes support plates of various types, namely at least one operation plate and at least one radiological support plate. A number of each type can be provided. Each plate type is specifically fashioned with regard to the hygienical and technical requirements associated with the procedure or procedures for which the plate is intended. As a result of the utilization of homogenous, identically fashioned fastening arrangements at each of the procedure-specific plates, as well as at the mechanism base (or at respective mechanism bases arranged in different rooms), it is possible to optionally arrange any of the support plates at any mechanism base in the inventive system. One or more connectors at the mechanism base itself supply required operational support such as current, gases etc. for implements or components, so that the devices necessary for the required treatment or examination can be connected. The inventive optional exchangeability of the respective support plates has the considerable advantage that the room containing the mechanism base can be used as an operation room, for example for emergencies, and can be used for radiological examinations as well. Apart from this significant advantage, another advantage is that only the homogenous type of fastening arrangement is needed, i.e., it is no longer necessary to provide different fastening arrangement for different plate-base-systems, as has been hitherto necessary in the prior art.

Inventively, each support plate situated at the mechanism base can be adjusted in height and is tiltable around at least one axis extending in the longitudinal direction and at least one axis extending in the transverse direction of the support plate. The inventive system provides this tilting possibility for each support plate type, i.e., the operation plate (which has conventionally mounted to tilt around its longitudinal axis and around one or more transverse axes) and the radiological support plate (which has not been conventionally mounted to as to be tillable) can now be more or less fully adjusted as needed. Apart from adjustment in height, rotation around the vertical base axis is also possible.

The radiological support plate can be inventively movable along an axis extending in the longitudinal direction relative to the support plate and along an axis extending in the transverse direction relative to the support plate. This floating mounting has the advantage that the patient can be moved relative to a radiological examination system, an X-ray device for example, in order to position the "region of interest" with respect to the image pickup system. It is expedient for the radiological support plate to be variable in length.

In another inventive embodiment, at least one electromechanical or hydraulic adjustment device is provided for the support plate situated at the mechanism base, and at least one electromechanical or hydraulic adjustment device for effecting tilting of the support device can be operated via a power supply and via a power supply independent thereof. The integration of the adjustment device in the mechanism base makes it possible to make the adjustment device accessible only at the side of the base, and each support plate can be moved by means of this adjustment device. Moreover, the operability of the adjustment device via an independent power supply has the advantage that a support plate that has been adjusted to a certain position can be brought again into an initial position, in which it can be removed from the mechanism base by means of the transport gurney, if the main power supply fails.

Furthermore, it is expedient for each support plate and base mechanism to have any crevices or recesses sealed, or for the plate to be sealingly encased, so that fluids cannot penetrate into the area of possible joint or motion mechanics or connections or into the area of the fastening arrangements. Such sealing or casing offers a secure protection against penetration by fluids such as blood or other body secretions and against fluids required in an interventional procedure, this being important for hygienical reasons. An encasing such as a lamella encasing can be provided at the mechanism base in order to prevent fluid from penetrating into the mechanism base region.

DESCRIPTION OF THE DRAWING

The single FIGURE is a schematic illustration showing the basic components, and manner of operation, of a support mechanism for an examination or treatment subject, in accordance with the principles of the present invention.

DESCRIPTION OF THE PREFERRED EMBODIMENTS

The FIGURE shows an inventive support mechanism system in the form of a basic diagram. The system has at least one mechanism base 1, which is firmly installed in a room, for example an operating room, or in a room for carrying out radiological examinations. A fastening arrangement 2 for fastening differently fashioned support plates 3a, 3b are provided at the upper end of the mechanism base 1. The support plate 3a is fashioned as a radiological support plate and is composed of radiation-transparent material over a major part of its length, so that exposures of a patient lying on it can be carried out by means of an image pickup system (not shown in greater detail), an X-ray device, for example. The radiological support plate 3a typically has areas of different width; and it is variable in length, as indicated by the double arrow A. Furthermore, it can be moved, while mounted at the mechanism base 1, in the direction of its longitudinal axis and in the direction of the transverse axis, i.e., it is mounted in a floating manner, as indicated by the crossed double arrow B. The support plate 3b is an operation plate, which, is fashioned for surgical procedure carrying out operations at a patient lying thereon.

Each of the support plates 3a, 3b has fastening arrangement 4a, 4b that are compatible with the fastening arrangement 2, these fastening arrangement 4a, 4b making it possible to detachably fasten the support plates 3a, 3b by cooperating with the fastening arrangement 2 at the mechanism base 1 (see arrows 1). The fastening arrangement 2, 4a, 4b can be of various types, for example locking elements, clamps, hook elements, etc. The fashioning of these is known, they are also utilized for the known exchangeable operation plates.

Furthermore, at least one adjustment device 5, which can be an electrical or a hydraulic adjustment device, is integrated at the mechanism base 1. This adjustment device 5 enables a movement of the fastening arrangement 2 and therefore of the attached support plate 3a or 3b, in the vertical direction, as indicated by the double arrow C. This means that each support plate 3a, 3b can be varied in height.

Moreover, the adjustment device 5 makes it possible to tilt the support plate 3a or 3b around a plate axis extending in the longitudinal direction as well as around a plate axis extending in the transverse direction, as indicted by the double arrows D and E. Furthermore, it is possible to rotate the mounted support plate 3a or 3b around the vertical mechanism base axis, as indicated by the double arrow F. The adjustment device 5 can be arbitrarily fashioned as long as it allows the desired movements. For example, it can be a scissor-type jack, whereby a motor and an rotating spindle are provided for adjusting purposes; lifting jacks or such devices are alternatively suitable.

The adjustment device 5 can cooperate with segmenting means (not shown in greater detail) at the operation plate 3b so that the operation plate 3b can be adjusted in segments. For this purpose, the operation plate 3b can be longitudinally segmented to that each segment be tilted around an axis 6 extending in the longitudinal direction of the plate. Additionally, for example the plate 3b can have two transverse axes 7a, 7b around which the adjacent plate sections can be tilted.

Furthermore, each of the support plates 3a, 3b is provided with corresponding sealing means such as coatings and encasings, which prevent fluids of any type from penetrating into critical areas, such as the area of the fastening arrangements or the base area. The mechanism base 1 also has a corresponding encasing (not shown).

Furthermore, connector 8 for one or more implements are provided at the mechanism base 1, for example for providing power supply or different gases as may be needed for treatment implements or components, so that required implements or components can be directly connected to the mechanism base. This is particularly necessary when surgical operations are carried out.

The inventive system also includes a transport gurney or cart 9, which also has a suitable fastening arrangement 10 cooperating with the fastening arrangements 4a, 4b provided at the side of each plate 3a, 3b, so that each support plates 3a, 3b can be transported to the mechanism base 1 or can be removed therefrom (see arrows 11) removed therefrom by the same transport gurney 9. In the described way, the inventive system utilizes fastening arrangements that are altogether homogenous and enable the variable exchangeability of the support plates 3a, 3b at the mechanism base 1 or at the transport gurney 9.

Although modifications and changes may be suggested by those skilled in the art, it is the intention of the inventors to embody within the patent warranted hereon all changes and modifications as reasonably and properly come within the scope of their contribution to the art.

We claim as our invention:

1. A support mechanism system comprising:
    at least two support plates, one of said support plates being an operation plate for conducting a surgical intervention at a subject adapted to be received on said operation plate, and a radiological support plate having at least one radiation-transparent region, each of said support plates having an identical plate fastening arrangement thereon;
    a mechanism base having a base fastening arrangement compatible with the identical plate fastening arrangements respectively on said support plates, said plate fastening arrangement receiving and coupling the plate fastening arrangement of one of said support plates at a time to mount said one of said support plates to said base mechanism; and a transport gurney adapted to receive any of said support plates to transport the support plate received on said transport gurney to and from said mechanism base.

2. A support mechanism system as claimed in claim 1 wherein said adjustment device is selected from the group consisting of electromechanical devices and hydraulic devices.

3. A support mechanism system as claimed in claim 1 further comprising an adjustment device for interacting with a support plate currently coupled to said base fastening arrangement for adjusting said support plate in height and for tilting said support plate around at least one axis parallel to a longitudinal direction of said support plate and around at least one axis parallel to a transverse direction of said support plate.

4. A support mechanism system as claimed in claim 3 wherein said adjustment device is an electrical power-consuming device operable via a mains power supply, and wherein said support mechanism system further comprises an independently operable power supply, connectable to said adjustment device, upon a power failure of said mains power supply.

5. A support mechanism system as claimed in claim 3 wherein said adjustment device is disposed in said mechanism base.

6. A support mechanism system as claimed in claim 1 further comprising an adjustment device which interacts with said radiological support plate when said radiological support plate is coupled to said base fastening arrangement for displacing said radiological support plate along an axis parallel to a longitudinal axis of said radiological support plate and along an axis parallel to a transverse axis of said radiological support plate.

7. A support mechanism system as claimed in claim 6 wherein said adjustment device is selected from the group consisting of electromechanical devices and hydraulic devices.

8. A support mechanism system as claimed in claim 6 wherein said adjustment device is an electrical power-consuming device operable via a mains power supply, and wherein said support mechanism system further comprises an independently operable power supply, connectable to said adjustment device, upon a power failure of said mains power supply.

9. A support mechanism system as claimed in claim 6 wherein said adjustment device is disposed in said mechanism base.

10. A support mechanism system as claimed in claim 1 wherein said radiological support plate is variable in length.

11. A support mechanism system as claimed in claim 1 further comprising a fluid-tight seal for each of support plates for preventing fluid entry into said support plate or into said plate fastening arrangement or said base fastening arrangement.

12. A support mechanism system as claimed in claim 1 further comprising a casing for preventing fluid entry into said mechanism base.

13. A support mechanism system as claimed in claim 12 wherein said casing comprises a lamella casing.

* * * * *